(12) United States Patent
Yani et al.

(10) Patent No.: US 6,989,243 B2
(45) Date of Patent: Jan. 24, 2006

US006989243B2

(54) METHOD OF DETERMINING THE CONCENTRATION OF AN ANALYTE IN A PHYSIOLOGICAL SAMPLE

(75) Inventors: Adva Yani, Milpitas, CA (US); Paing C. Huang, San Francisco, CA (US)

(73) Assignee: LifeScan, Inc., Milpitas, CA (US)

( * ) Notice: Subject to any disclaimer, the term of this patent is extended or adjusted under 35 U.S.C. 154(b) by 376 days.

(21) Appl. No.: 10/155,949

(22) Filed: May 24, 2002

(65) Prior Publication Data

US 2002/0192733 A1 Dec. 19, 2002

Related U.S. Application Data

(62) Division of application No. 09/497,631, filed on Feb. 2, 2000, now Pat. No. 6,485,923.

(51) Int. Cl.
*C12Q 1/54* (2006.01)

(52) U.S. Cl. .......................... 435/14; 422/56
(58) Field of Classification Search ................ 435/14, 435/259; 422/56
See application file for complete search history.

(56) References Cited

U.S. PATENT DOCUMENTS

| | | | |
|---|---|---|---|
| 4,297,238 A | * 10/1981 | Vormbrock et al. | 436/17 |
| 4,551,427 A | * 11/1985 | Draeger et al. | 435/14 |
| 5,258,047 A | 11/1993 | Tokisue et al. | 29/25.01 |
| 5,278,047 A | * 1/1994 | Lilja et al. | 435/14 |
| 5,541,117 A | 7/1996 | Karl et al. | |
| 5,563,042 A | 10/1996 | Phillips et al. | 435/14 |
| 5,705,357 A | 1/1998 | Kissel et al. | |
| 5,709,837 A | 1/1998 | Mori et al. | |
| 5,753,452 A | 5/1998 | Smith | 435/14 |
| 5,789,255 A | 8/1998 | Yu | 536/95 |
| 5,843,691 A | 12/1998 | Douglas et al. | 435/14 |
| 5,866,349 A | 2/1999 | Lilja et al. | 435/13 |
| 5,891,731 A | 4/1999 | Akai et al. | |
| 5,968,836 A | 10/1999 | Matzinger et al. | 436/169 |
| 5,972,294 A | 10/1999 | Smith et al. | 422/58 |
| 6,027,692 A | * 2/2000 | Galen et al. | 422/82.05 |
| 6,485,923 B1 | * 11/2002 | Yani et al. | 435/14 |

FOREIGN PATENT DOCUMENTS

| | | |
|---|---|---|
| DE | 3424355 A1 | 1/1985 |
| DE | 4229477 A1 | 3/1994 |
| DE | 0695936 A2 | 2/1996 |
| DE | 0708335 A2 | 4/1996 |
| DE | 0840124 A2 | 5/1998 |
| EP | 0 638 805 | 2/1995 |
| JP | 62296987 | 12/1987 |
| JP | 03180762 | 8/1991 |
| WO | 90/12889 | 11/1990 |
| WO | 90/12890 | 11/1990 |

* cited by examiner

*Primary Examiner*—Ralph Gitomer
(74) *Attorney, Agent, or Firm*—Carol M. LaSalle; Bozicevic, Field & Francis, LLP

(57) ABSTRACT

Methods for determining the concentration of an analyte, e.g. glucose, in a physiological sample, are provided. The subject methods use reagent test strips which include one or more members of an analyte oxidation signal producing system and at least one hemolyzing agent. The subject methods are particularly suited for use in the detection of blood glucose concentrations.

5 Claims, 4 Drawing Sheets

—— 25% Hct  y = 0.1121 + 0.016565x  $R^2$ = 0.99685
- - - 43% Hct  y = 0.18819 + 0.015358x  $R^2$ = 0.99933
- - - - 60% Hct  y = 0.3262 + 0.013394x  $R^2$ = 0.99923

—— 25% Hct  y = 0.357 + 0.011587x  $R^2$ = 0.99686
- - - 43% Hct  y = 0.33679 + 0.011989x  $R^2$ = 0.99838
- - - - 60% Hct  y = 0.38644 + 0.011436x  $R^2$ = 0.99857

METHOD OF DETERMINING THE CONCENTRATION OF AN ANALYTE IN A PHYSIOLOGICAL SAMPLE

CROSS-REFERENCE

This application is a divisional application of U.S. patent application Ser. No. 09/497,631, filed Feb. 2, 2000 now U.S. Pat. No. 6,485,932, which is incorporated herein by reference in its entirety and to which application we claim priority under 35 USC §120.

INTRODUCTION

1. Field of the Invention

The field of this invention is analyte determination, particular blood analyte determination and more particularly blood glucose determination.

2. Background

Analyte detection in physiological fluids, e.g. blood or blood derived products such as plasma, is of ever increasing importance to today's society. Analyte detection assays find use in a variety of applications and settings, including the clinical laboratory testing, home testing, etc., where the results of such testing play a prominent role in diagnosis and management in a variety of disease conditions. Analytes of interest include glucose for diabetes management, cholesterol for monitoring cardiovascular conditions, and the like. In response to this growing importance of analyte detection, a variety of analyte detection protocols and devices for both clinical and home use have been developed.

Many analyte detection assays are based on the production of hydrogen peroxide and the subsequent detection thereof. Analytes that may be detected using such assays include: cholesterol, triglycerides, glucose, ethanol and lactic acid. For example, glucose is quantitated using such assays by first oxidizing glucose with glucose oxidase to produce gluconic acid and hydrogen peroxide. The resultant hydrogen peroxide, in conjunction with a peroxidase, causes the conversion of one or more organic substrates, i.e. an indicator, into a chromogenic product, which product is then detected and related to the glucose concentration in the initial sample.

Hydrogen peroxide based assays, such as the glucose assay described above, are subject to problems which result from the presence of erythrocyte components, e.g. catalase, that interfere with the hydrogen peroxide based reaction and therefore alter (for example reduce) the signal that is ultimately obtained and used to derive the analyte concentration. As such, many different protocols have been developed which are designed to at least reduce the potential analytical error that is introduced in the assay through the release of interfering erythrocyte components via hemolysis. Such protocols include: filtration, filtration combined with the addition of inhibitors, filtration and trapping of erythrocytes, and the use of asymmetric non-hemolyzing membranes.

While such methods can partially remove the analytical error introduced by hemolysis, they are not entirely satisfactory. For example, filtration typically requires longer assay times and larger sample sizes than is desirable.

As such, there is continued interest in the development of new devices and methods for use in analyte detection. Of particular interest would be the development such a device and method which minimized the analytical error originating from hemolysis and yet provided a rapid assay time from a small sample volume.

Relevant Literature

U.S. Patent documents of interest include: U.S. Pat. Nos. 4,297,238; 5,258,047; 5,563,042; 5,753,452; 5,789,255; 5,843,691; 5,866,349; 5,968,836 and 5,972,294. Also of interest are: WO 90/12889; WO 90/12890; JP 3180762; JP 62296987; and EP 0 638 805.

SUMMARY OF THE INVENTION

Reagent test strips and methods for their use in the determination of the concentration of an analyte, e.g. glucose, in a physiological sample are provided. The subject reagent test strips include one or more members of an analyte oxidation signal producing system and at least one hemolyzing agent. The subject reagent test strips and methods are particularly suited for use in the detection of blood glucose concentrations. Also provided are kits that include the subject test strips for use in practicing the subject methods.

DESCRIPTION OF THE SPECIFIC EMBODIMENTS

Figure 1:
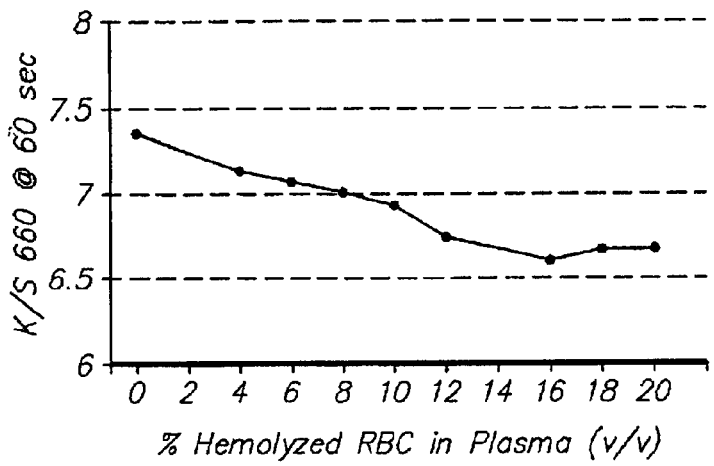
FIG. 1 provides a graphical representation of the effect of hemolysate on test response.

Reagent test strips for use in the determination of the concentration of an analyte, e.g. glucose, in a physiological sample, e.g. blood, are provided. The subject test strips include a porous matrix, one or more members of an analyte oxidation signal producing system and at least one hemolyzing agent. In using the subject test strips for analyte concentration determination, a physiological sample is applied to the test strip. Next, the appearance of a chromogenic product of the signal producing system is detected and related to the concentration of the analyte in the sample. Also provided by the subject invention are kits for practicing the subject methods, where the kits at least include the subject reagent test strips. In further describing the subject invention, the subject test strips and methods for their use are discussed in greater detail, followed by a review of the subject kits.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, singular references include the plural, unless the context clearly dictates otherwise. Unless defined otherwise, all technical and scientific terms used herein have the same meaning as commonly understood to one of ordinary skill in the art to which this invention belongs.

Reagent Test Strips

As summarized above, the reagent test strips of the subject invention are characterized by having at least the following components: a porous matrix; one or more members of an analyte oxidation signal producing system; and at least one hemolyzing agent. Each one of these components is now described separately in greater detail.

The Porous Matrix

The matrix that is employed in the subject test strips is an inert porous matrix which provides a support for the various members of the signal producing system, described infra, as well as the light absorbing or chromogenic product produced by the signal producing system, i.e. the indicator. The inert porous matrix is configured to provide a location for physiological sample, e.g. blood, application and a location for detection of the light-absorbing product produced by the indicator of the signal producing system. As such, the inert porous matrix is one that is permissive of aqueous fluid flow through it and provides sufficient void space for the chemical reactions of the signal producing system to take place. A number of different porous matrices have been developed for use in various analyte detection assays, which matrices may differ in terms of materials, pore sizes, dimensions and the like, where representative matrices include those described in: U.S. Pat. Nos. 4,734,360; 4,900,666; 4,935,346; 5,059,394; 5,304,468; 5,306,623; 5,418,142; 5,426,032; 5,515,170; 5,526,120; 5,563,042; 5,620,863; 5,753,429; 5,573,452; 5,780,304; 5,789,255; 5,843,691; 5,846,486; 5,968,836 and 5,972,294; the disclosures of which are herein incorporated by reference. In principle, the nature of the porous matrix is not critical to the subject test strips and therefore is chosen with respect to the other factors, including the nature of the instrument which is used to read the test strip, convenience and the like. As such, the dimensions and porosity of the test strip may vary greatly, where the matrix may or may not have a porosity gradient, e.g. with larger pores near or at the sample application region and smaller pores at the detection region. Materials from which the matrix may be fabricated vary, and include polymers, e.g. polysulfone, polyamides, cellulose or absorbent paper, and the like, where the material may or may not be functionalized to provide for covalent or non-covalent attachment of the various members of the signal producing system, described in greater detail infra.

The Signal Producing System

In addition to the porous matrix, the subject test strips further include one or more members of a signal producing system which produces a detectable product in response to the presence of analyte, which detectable product can be used to derive the amount of analyte present in the assayed sample. In the subject test strips, the one or more members of the signal producing system are associated, e.g. covalently or non-covalently attached to, at least a portion of (i.e. the detection region) the porous matrix, and in many embodiments to substantially all of the porous matrix.

The signal producing system is an analyte oxidation signal producing system. By analyte oxidation signal producing system is meant that in generating the detectable signal from which the analyte concentration in the sample is derived, the analyte is oxidized by a suitable enzyme to produce an oxidized form of the analyte and a corresponding or proportional amount of hydrogen peroxide. The hydrogen peroxide is then employed, in turn, to generate the detectable product from one or more indicator compounds, where the amount of detectable product producing by the signal producing system, i.e. the signal, is then related to the amount of analyte in the initial sample. As such, the analyte oxidation signal producing systems present in the subject test strips are also correctly characterized as hydrogen peroxide based signal producing systems.

As indicated above, the hydrogen peroxide based signal producing systems include an enzyme that oxidizes the analyte and produces a corresponding amount of hydrogen peroxide, where by corresponding amount is meant that the amount of hydrogen peroxide that is produced is proportional to the amount of analyte present in the sample. The specific nature of this first enzyme necessarily depends on the nature of the analyte being assayed but is generally an oxidase. As such, the first enzyme may be: glucose oxidase (where the analyte is glucose); cholesterol oxidase (where the analyte is cholesterol); alcohol oxidase (where the analyte is alcohol); lactate oxidase (where the analyte is lactate) and the like. Other oxidizing enzymes for use with these and other analytes of interest are known to those of skill in the art and may also be employed. In those preferred embodiments where the reagent test strip is designed for the detection of glucose concentration, the first enzyme is glucose oxidase. The glucose oxidase may be obtained from any convenient source, e.g. a naturally occurring source such as *Aspergillus niger* or *Penicillum*, or recombinantly produced.

The second enzyme of the signal producing system is an enzyme that catalyzes the conversion of one or more indicator compounds into a detectable product in the presence of hydrogen peroxide, where the amount of detectable product that is produced by this reaction is proportional to the amount of hydrogen peroxide that is present. This second enzyme is generally a peroxidase, where suitable peroxidases include: horseradish peroxidase (HRP), soy peroxidase, recombinantly produced peroxidase and synthetic analogs having peroxidative activity and the like. See e.g., Y. Ci, F. Wang; Analytica Chimica Acta, 233 (1990), 299–302.

The indicator compound or compounds, e.g. substrates, are ones that are either formed or decomposed by the hydrogen peroxide in the presence of the peroxidase to produce an indicator dye that absorbs light in a predetermined wavelength range. Preferably the indicator dye absorbs strongly at a wavelength different from that at which the sample or the testing reagent absorbs strongly. The oxidized form of the indicator may be the colored, faintly-colored, or colorless final product that evidences a change in color of the testing side of the membrane. That is to say, the testing reagent can indicate the presence of glucose in a sample by a colored area being bleached or, alternatively, by a colorless area developing color.

Indicator compounds that are useful in the present invention include both one- and two-component chromogenic substrates. One-component systems include aromatic amines, aromatic alcohols, azines, and benzidines, such as tetramethyl benzidine-HCl. Suitable two-component systems include those in which one component is MBTH, an MBTH derivative (see for example those disclosed in U.S. patent application Ser. No. 08/302,575, incorporated herein by reference), or 4-aminoantipyrine and the other component is an aromatic amine, aromatic alcohol, conjugated amine, conjugated alcohol or aromatic or aliphatic aldehyde. Exemplary two-component systems are 3-methyl-2-benzothiazolinone hydrazone hydrochloride (MBTH) combined with 3-dimethylaminobenzoic acid (DMAB); MBTH combined with 3,5-dichloro-2-hydroxybenzene-sulfonic acid (DCHBS); and 3-methyl-2-benzothiazolinone hydrazone N-sulfonyl benzenesulfonate monosodium (MBTHSB) combined with 8-anilino-1 naphthalene sulfonic acid ammonium (ANS). In certain embodiments, the dye couple MBTHSB-ANS is preferred.

In yet other embodiments, signal producing systems that produce a fluorescent detectable product (or detectable non-fluorescent substance, e.g. in a fluorescent background) may be employed, such as those described in: Kiyoshi Zaitsu, Yosuke Ohkura: New fluorogenic substrates for Horseradish Peroxidase: rapid and sensitive assay for hydrogen peroxide and the Peroxidase. Analytical Biochemistry (1980) 109, 109–113.

Hemolyzing Agent

A feature of the subject reagent test strips is the presence of at least one hemolyzing reagent. By hemolyzing agent is meant an agent that is capable of lysing erythrocytes or red blood cells. Any convenient hemolyzing agent may be employed, where a variety of different hemolyzing agents are known to those of skill in the art. Representative hemolyzing agents of interest include ionic surface-active agents, both anionic and cationic, and non-ionic surface active agents, where particular surfactants of interest include: sodium dodecylsulfate, cetyltrimethylammonium bromide, laurylsarcosine or tauroglycocholate, alkylphenol polyglycol ethers, e.g. polyoxyethylene-10-octylphenol ether (Triton® X 100), polyoxyethylene-7.8-octylphenol ether (Triton® X 114), polyoxyethylene-10-nonylphenol ether (Renex®690), polyoxyethylene-9-nonylphenol ether (Renex® 680); N-hexadecyltrimetheyl ammonium chloride; Brij-58; Lubrol PX, and the like. Other agents of interest include:

phospholipases, hemolyzing saponins, compounds of hydrophilic mono-, di-, or trisaccharides and aliphatic hydrocarbons having 10 to 16 carbon atoms (See e.g. PCT/SE90/00272, the disclosure of which is herein incorporated by reference) colloidal silica, silicic acid, hydroxyapatite crystals, and the like.

The subject test strips may include one type of hemolyzing agent, or may include two or more different types of hemolyzing agents, e.g. a plurality of different hemolyzing agents. Where the subject test strips include more than one hemolyzing agent, i.e. a plurality of hemolyzing agents, the strips generally include from two to five different hemolyzing agents, and usually from two to four different hemolyzing agents. The total amount of the one or more hemolyzing agents that is included in the test strip is chosen to produce hemolysis which is equivalent to at least about 5% hemolysate by volume in the sample usually at least about 8% and in many embodiments at least about 10% hemolysate in the sample, e.g. plasma fraction, that is ultimately present in the detection region following sample application. In certain embodiments, the amount of hemolyzing agent(s) present in the test strip is sufficient to provide from about 5 to 40, usually from about 8 to 30 and more usually from about 10 to 20% (v/v) hemolysate in the sample, e.g. plasma fraction, that is present in the detection region of the strip during use. The amount of hemolyzing agent required to yield the requisite hemolysate in the sample may readily be determined empirically by those of skill in the art.

The reagent test strips of the subject invention can be prepared using any convenient method. One convenient means of preparing the subject test strips is to immerse a porous matrix into to one or more fluid compositions that comprise the various reagents that are to be associated with the matrix in the final test strip. The fluid compositions are generally aqueous compositions that include one or more of the requisite reagents and, optionally, other components, including cosolvents (e.g. organic cosolvents such as methanol, ethanol isopropyl alcohol) and the like. In such embodiments, the concentration of oxidase, e.g. glucose oxidase, in the fluid composition into which the porous matrix is immersed or dipped typically ranges from about 1500 U/mL to 800 U/mL, usually from about 990 U/mL to 970 U/mL; the concentration of peroxidase typically ranges from about 1500 U/mL to 800 U/mL and usually from about 1050 U/mL to 900 U/mL; and the concentration of hemolyzing agent(s) typically ranges from about 0.1% (w/v) to 0.5% (w/v), usually from about 0.15% (w/v) to 0.25% (w/v). A more detailed representative protocol on how to prepare the subject reagent test strips is provided in the Experimental Section, infra.

Methods

Also provided by the subject invention are methods of using the subject test strips to determine the concentration of an analyte in a physiological sample. A variety of different analytes may be detected using the subject test strips, where representative analytes include glucose, cholesterol, lactate, alcohol, and the like. In many preferred embodiments, the subject methods are employed to determine the glucose concentration in a physiological sample. While in principle the subject methods may be used to determine the concentration of an analyte in a variety of different physiological samples, such as urine, tears, saliva, and the like, they are particularly suited for use in determining the concentration of an analyte in blood or blood fractions, e.g. blood derived samples, and more particularly in whole blood.

In practicing the subject methods, the first step is to apply a quantity of the physiological sample to the test strip, where the test strip is described supra. The amount of physiological sample, e.g. blood, that is applied to the test strip may vary, but generally ranges from about 2 $\mu$L to 40 $\mu$L, usually from about 51 $\mu$L to 20 $\mu$L. Because of the nature of the subject test strip, where blood glucose concentration if of interest, the blood sample size that is applied to the test strip may be relatively small, ranging in size from about 2 $\mu$L to 40 $\mu$L, usually from about 5 $\mu$L to 20 $\mu$L. Where blood is the physiological sample, blood samples of a variety of different hematocrits may be assayed with the subject methods, where the hematocrit may range from about 20% to 65%, usually from about 25% to 60%.

Following application of the sample to the test strip, the sample is allowed to react with the members of the signal producing system to produce a detectable product that is present in an amount proportional to the initial amount present in the sample. The amount of detectable product, i.e. signal produced by the signal producing system, is then determined and related to the amount of analyte in the initial sample. In certain embodiments, automated instruments that perform the above mentioned detection and relation steps are employed. The above described reaction, detection and relating steps, as well as instruments for performing the same, are further described in U.S. patent application Ser. Nos. 4,734,360; 4,900,666; 4,935,346; 5,059,394; 5,304,468; 5,306,623; 5,418,142; 5,426,032; 5,515,170; 5,526,120; 5,563,042; 5,620,863; 5,753,429; 5,573,452; 5,780,304; 5,789,255; 5,843,691; 5,846,486; 5,968,836 and 5,972,294; the disclosures of which are herein incorporated by reference. In the relation step, the derived analyte concentration takes into account the constant contribution of competing reactions to the observed signal, e.g. by calibrating the instrument accordingly.

Because of the presence of hemolyzing agent on the test strips employed in the subject methods, the results that are obtained by the subject methods are substantially, if not completely, free of analytical error that arises in configurations that lack a hemolyzing agent on the test strip, where the analytical error is a result of the presence of erythrocyte based interfering components, e.g. catalase, hemoglobin, glutathione peroxidase and the like. As such, the subject methods are substantially, if not completely, free of the hematocrit effect which can introduce analytical error to analyte measurements made with other detection devices and protocols. In addition, because of the presence of the hemolyzing agent(s) on the test strip, results are obtained in a rapid manner, where results can be obtained in less than about 20 seconds, usually less than about 30 seconds and more usually less than about 40 seconds following application of the sample to the test strip.

Kits

Also provided by the subject invention are kits for use in practicing the subject methods. The kits of the subject invention at least include a reagent test strip that includes a hemolyzing agent, as described above. The subject kits may further include a means for obtaining a physiological sample. For example, where the physiological sample is blood, the subject kits may further include a means for obtaining a blood sample, such as a lance for sticking a finger, a lance actuation means, and the like. In addition, the subject kits may include a control solution or standard, e.g. a glucose control solution that contains a standardized concentration of glucose. In certain embodiments, the kits also include an automated instrument, as described above, for detecting the amount of product produced on the strip following sample application and related the detected product to the amount of analyte in the sample. Finally, the kits include instructions for using the subject reagent test strips in the determination of an analyte concentration in a physiological sample. These instructions may be present on one or more of the packaging, a label insert, containers present in the kits, and the like.

The following examples are offered by way of illustration and not by way of limitation.

Experimental

A. Preparation of Test Strips

The porous side of a 0.35 μm polysulfone membrane (reaction matrix—obtained from U.S. Filter, San Diego, Calif.) was submerged in the aqueous dip shown in Table 1 until saturated. It was removed from the dip and the excess reagent was squeezed off with a glass rod. The strip was then hung inside an air circulating oven at 56° C. for about 10 minutes to dry, after which time the strip was removed and dipped into the organic dip described in Table 2 until saturated. It was then dried again as in the previous step. The resulting strip was fashioned into the desired shape for testing.

TABLE 1

| Ingredient | Amount |
| --- | --- |
| H$_2$O | 25 mL |
| Citric Acid | 282 mg |
| Trisodium Citrate | 348 mg |
| Mannitol | 250 mg |
| EDTA | 21 mg |
| Gantrez (obtained from GAF, New York, New York) | 112.5 mg |
| Crotein (obtained from CRODA, New York, New York) | 360 mg |
| Glucose Oxidase (126 U/mg) | 234.5 mg |
| Horse Radish Peroxidase (505 U/mg) | 62 mg |
| Carbapol 910 (0.11 mg/mL in acetonitrile) (obtained from BF Goodrich, Clevelend Ohio) | 1.25 mL |
| 0.1 M disodium citrate | 3.75 mL |

TABLE 2

| Ingredient | Amount |
| --- | --- |
| MeOH/EtOH/H$_2$O (17.5/52.5/30) | 9.54 mL |
| MBTHSB Meta[3-methyl-2-benzothiazolinone hydrazone]N-sulfonyl benzenesulfonate monosodium | 38.8 mg |
| ANS | 54 mg |
| MAPHOS 60A (20% in the above solvent) (PPG/Mazer, Gurnee, Illinios) | 0.46 mL |
| ⊥hemolyzing surfactant or control | 0 to 50 mg |

⊥Hemolyzing Surfactants:
control = 0 g = 0%
N-hexadecyltrimethylammonium chloride(CTAC) = 7.5 mg = 0.075%
N-hexadecyltrimethylammonium chloride(CTAC) = _25 mg = 0.25%
Triton X-100 25 mg = 0.25%
Brij 58 = 50 mg = 0.5%
Lubrol PX = 50 mg = 0.5%

B. Testing

SureStep® strip configurations were used for testing of glucose response. Reflectance data was collected on modified SureStep® meters. Reflectance spectral data was acquired using Macbeth Color Eye (GretagMacbeth, New Windsor, N.Y.). Blood samples are as noted.

III. Results

Figure 2A:
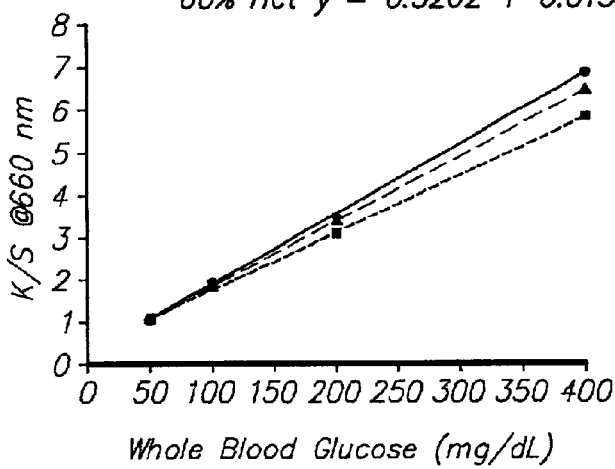
FIGS. 2a provides a graphical representation of the effect of hematocrit on test response in the absence of a hemolyzing agent, while FIG. 2b provides a graphical representation of the effect of hematocrit on test response in the presence of 0.25% CTAC.
Figure 2B:
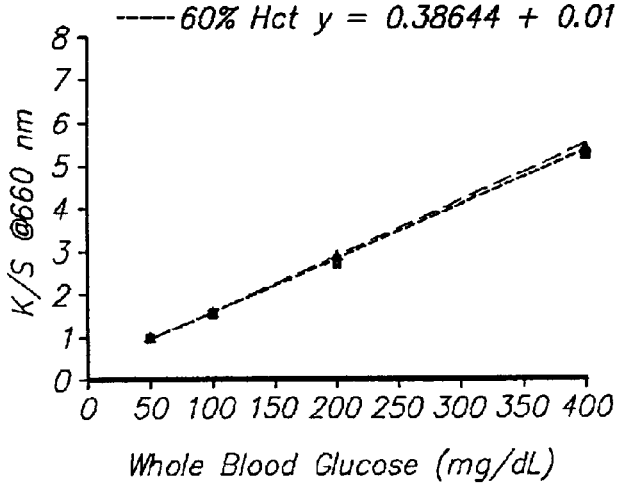
Figure 3:
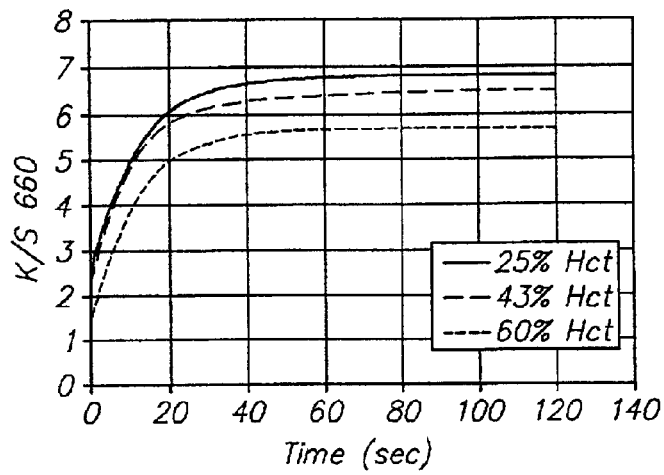
FIGS. 3 and 4 provide graphical representations of the test response and reaction kinetics observed at a whole blood glucose concentration of 390 mg/dL in the absence and presence of 0.25% CTAC.
Figure 4:
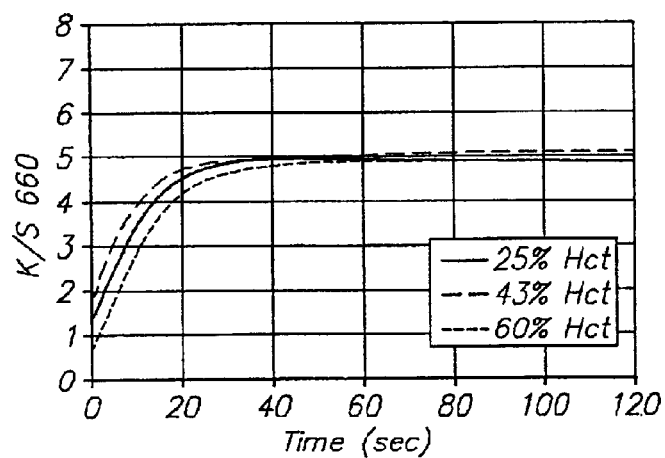
Figure 5:
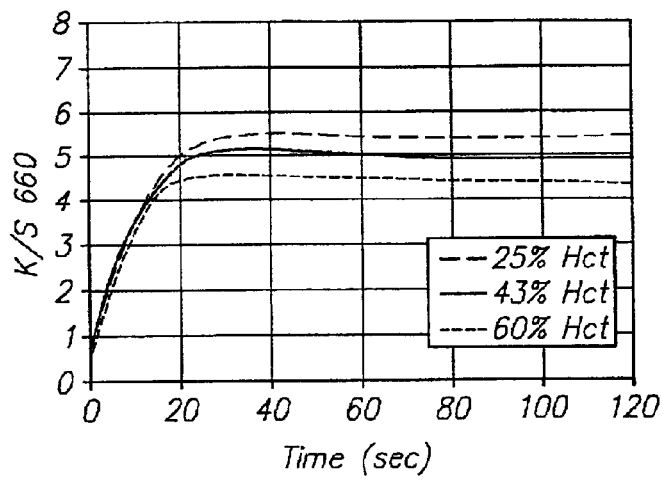
FIGS. 5 and 6 provide graphical representations of the test response and reaction kinetics observed at a whole blood glucose concentration of 390 mg/dL in the absence and presence of 0.25% Triton X-100.
Figure 6:
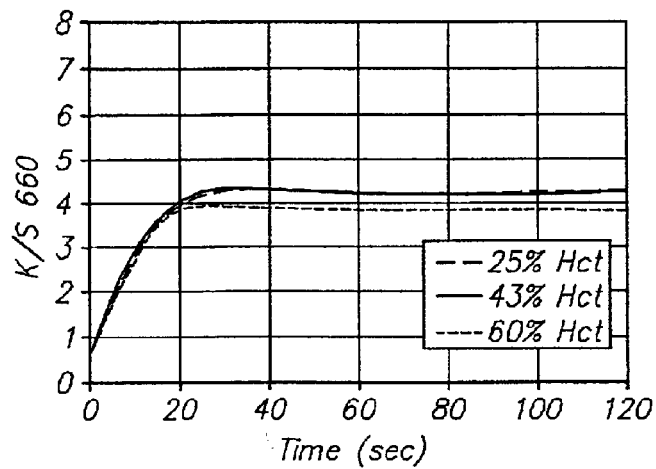
Figure 7:
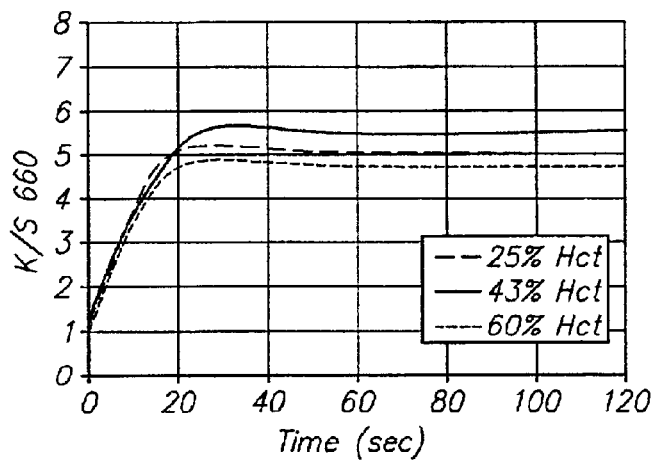
FIGS. 7 and 8 provide graphical representations of the test response and reaction kinetics observed at a whole blood glucose concentration of 390 mg/dL in the absence and presence of 0.50% Brij-58.
Figure 8:
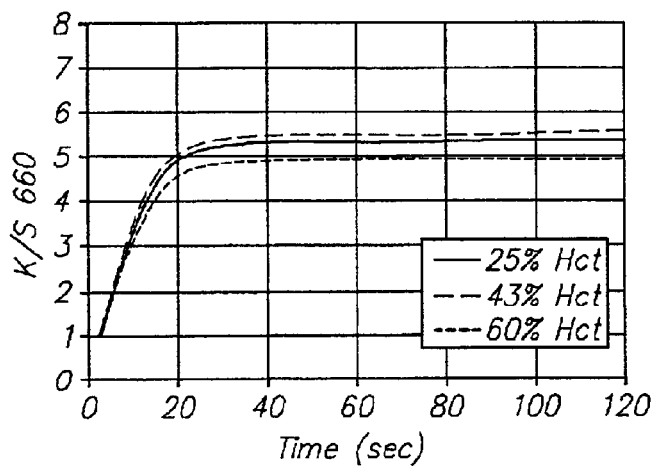
Figure 9:
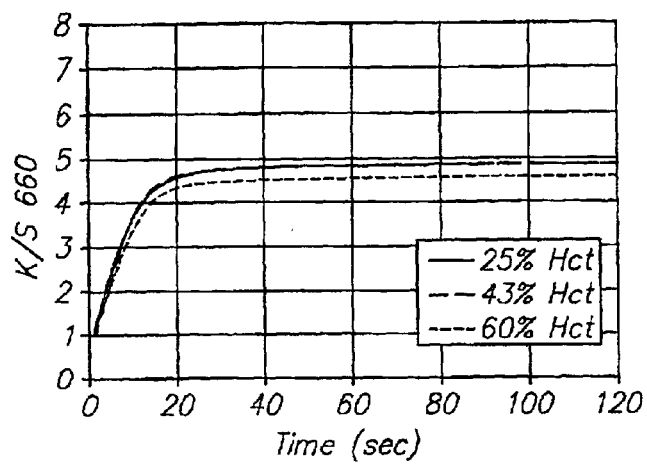
FIG. 9 provides a graphical representation of the test response and reaction kinetics observed at a whole blood glucose concentration of 390 mg/dL in the presence of 0.50% Lubrol PX.
Figure 10:
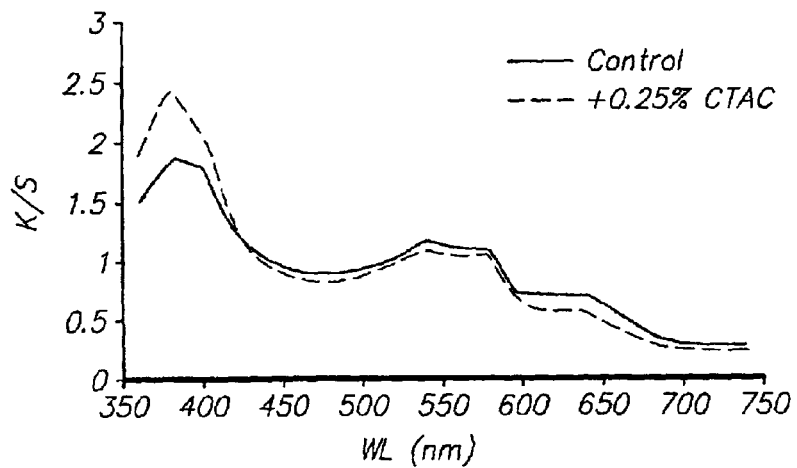
FIG. 10 provides a graphical representation of the variation in observed K/S in the presence and absence of 0.25% CTAC in 60% Hct blood having a 0.0 mg/dL glucose concentration.
Figure 11:
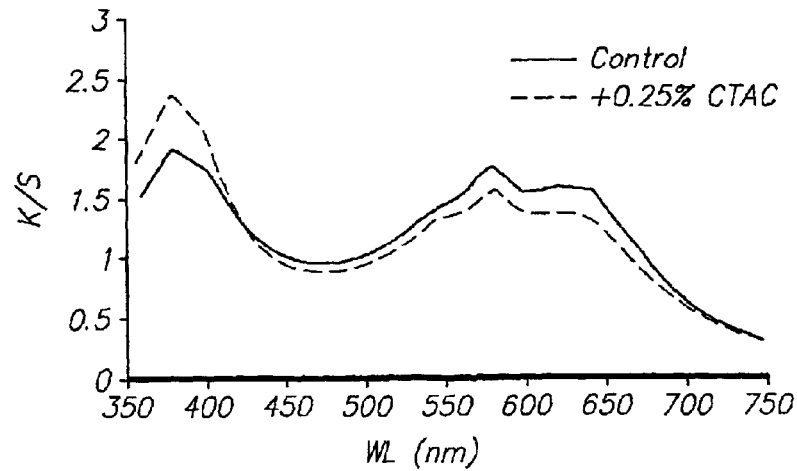
FIG. 11 provides a graphical representation of the variation in observed K/S in the presence and absence of 0.25% CTAC in 60% Hct blood having a 30 mg/dL glucose concentration.

FIG. 1 shows the effect of hemolysis on the meter response. FIG. 1 demonstrates that most of the decrease in color formation due to competing reactions is produced by hemolysis in the rang of 0 to 8% and the response remains constant at the range of 10 to 20% hemolysis. By adding a certain amount of hemolyzing surfactant to the reagent formulation, one can ensure that blood samples applied to the strip are hemolyzed in the range of 10 to 20% across the range of potential hematocrit. This range of hemolysis allows for analyte calibration that is unaffected by the level of hematocrit. See FIGS. 2a and 2b. Endpoint is achieved faster in the presence of hemolysate, since some of the hydrogen peroxide (produced by the peroxidase reaction), is being consumed by reactions with hemolysate components. See FIGS. 3 and 4. FIGS. 3 and 4 provide the observed test response and reaction kinetics for a control and 0.25% CTAC strip at a whole blood concentration of 390 mg/dL. FIGS. 5 and 6 provide the observed test response and reaction kinetics for a control and 0.25% Triton X-100 strip at a whole blood concentration of 390 mg/dL. FIGS. 7 and 8 provide the observed test response and reaction kinetics for a control and 0.50% Brij-58 strip at a whole blood concentration of 390 mg/dL; while FIG. 9 provides the observed test response and reaction kinetics for a 0.50% Lubrol PX strip at a whole blood glucose concentration of 390 mg/dL. FIGS. 10 and 11 demonstrate the hemolyzing effect of the CTAC surfactants as indicated by a higher absorbance at the hemoglobin's Soret band (around 400 nm) in the presence of CTAC. Visual confirmation of the test results is a beneficial feature offered by the SureStep system. FIG. 10 shows that hemolysis at the range required in this invention does not cause increased blood color (red appearance) in the visual range even when high hematocrit sample is applied to the strip, and therefore will not interfere with the visual confirmation of the test results.

It is evident from the above results and discussion that the subject invention provides for a significant improvement in hematocrit performance with respect to analytical error results from erythrocyte based interfering components. In addition, the subject invention provides for these improved results without requiring an initially large physiological sample or a long assay time. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of determining a analyte concentration in a physiological sample, said method comprising:
   (a) applying said physiological sample to a test strip comprising:
      (i) a porous matrix;
      (ii) at least one member of an analyte oxidation signal producing system; and
      (iii) at least one hemolyzing agent, wherein said hemolyzing agent is present in an amount sufficient to produce hemolysis which is equivalent to a hemolysate concentration in a physiological sample applied to said porous matrix in an amount ranging from about 5 to 20% by volume;
   (b) detecting a signal produced by said signal producing system; and
   (c) relating said detected signal to the analyte concentration in said physiological sample.

2. The method according to claim 1, wherein said analyte is glucose.

3. The method according to claim 1, wherein said physiological sample is whole blood.

4. The method according to claim 1, wherein said hemolyzing agent is present in an amount sufficient to produce hemolysis which is equivalent to the hemolysate concentration in a physiological sample applied to said porous matrix in an amount ranging from about 5 to 20% by volume.

5. The method according to claim 1, wherein said detecting and relating steps are carried out by an automated instrument.

* * * * *